US00PP13575P2

(12) United States Plant Patent
Skotak, Jr.

(10) Patent No.: US PP13,575 P2
(45) Date of Patent: Feb. 18, 2003

(54) GUZMANIA PLANT NAMED 'DURAHURO'

(76) Inventor: Chester Skotak, Jr., Apdo. 652-4050, Alajuela (CR)

( * ) Notice: Subject to any disclaimer, the term of this patent is extended or adjusted under 35 U.S.C. 154(b) by 0 days.

(21) Appl. No.: 09/962,593

(22) Filed: Sep. 26, 2001

(30) Foreign Application Priority Data

Mar. 8, 2001 (EP) ..... 2001/0432

(51) Int. Cl.[7] ..... A01H 5/00
(52) U.S. Cl. ..... Plt./371
(58) Field of Search ..... Plt./371

*Primary Examiner*—Kent L. Bell
(74) *Attorney, Agent, or Firm*—Foley & Lardner

(57) ABSTRACT

A new and distinct Guzmania plant named 'Durahuro' characterized by its short leaf size; erect inflorescence; thick inflorescence; and bright red floral bracts upper side red, RHS 47A, under side red, RHS 42A to RHS 42B.

2 Drawing Sheets

LATIN NAME OF THE GENUS AND SPECIES OF THE PLANT CLAIMED

Guzmania hybrid.

VARIETY DENOMINATION

'Durahuro'.

BACKGROUND OF THE INVENTION

The present invention comprises a new and distinct cultivar of Guzmania plant, hereinafter referred to by the cultivar name 'Durahuro'. The genus Guzmania is a member of the family Bromeliaceae.

Guzmania comprise a genus of over 100 species of herbaceous evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from the yellow through orange but may also include flame red and red-purple. White or yellow, tubular, three petalled flowers may also appear on a stem or within the leaf rosette but are usually short lived.

Guzmania may be advantageously grown as potted plants for greenhouse or home use. Desirably the plants are shaded from direct sunlight during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in an appropriate soil or bark mixture.

The new cultivar 'Durahuro' is the product of a planned breeding program and originated by the inventor Chester Skotak Jr. from a cross made during such program in 1993 in Alajuela, Costa Rica. The female or seed parent and the male or pollen parent are unknown Guzmania varieties. 'Durahuro' was selected as one plant growing among seedlings of the above stated cross. The selection comprising the new variety was chosen after commencement of flowering in 1994.

The new cultivar was asexually propagated by cuttings by Deroose Plants in Evergem, Belgium, beginning in July, 1994. Asexual propagation by tissue culture was initiated in 1997. Continuous asexual propagation has demonstrated that the combination of characteristics as herein disclosed for the new cultivar 'Durahuro' are firmly fixed, reproduce true to type, and are retained through successive generations of asexual reproduction.

BRIEF DESCRIPTION OF THE INVENTION

The following traits have been repeatedly observed and are determined to be basic characteristics of 'Durahuro' which in combination distinguish this Guzmania as a new and distinct cultivar:

1. Short leaf size;

2. Erect inflorescence;

3. Thick inflorescence; and

4. Bright red floral bracts, upper side red, RHS 47A, under side red, RHS 42A to RHS 42B.

'Durahuro' has not been observed under all possible environmental conditions. The phenotype of the new cultivar may vary significantly with variations in environment such as temperature, light intensity, and day length without any change in genotype.

Of the many commercial cultivars known to the present inventor, the most similar in comparison to 'Durahuro' is the cultivar 'Grand Prix' (unpatented). In comparison to 'Grand Prix', the leaves of 'Durahuro' are considerably shorter. The flowers of 'Durahuro' are erect contrary to the flowers of 'Grand Prix'. The flowers of Guzmania 'Durahuro' grow thicker and are brighter red than the flowers of Guzmania 'Grand Prix'.

BRIEF DESCRIPTION OF THE DRAWING

The accompanying photographic drawings show a 19-month-old 'Durahuro' plant in an 11 cm pot, propagated by tissue culture following growth under appropriate growing conditions, with colors being as true as possible with illustrations of this type.

The first drawing depicts a side view of a typical plant of 'Durahuro'.

The second drawing is a close up view of the inflorescence and foliage characteristics of 'Durahuro'.

DETAILED BOTANICAL DESCRIPTION

The following observations, measurements and values describe plants grown in Evergem, Belgium, under greenhouse conditions which closely approximate those generally used in horticultural practice. Plants described were 19 months old grown in an 11 cm pot.

'Durahuro' is grown in a commercial greenhouse under 21 degrees Celsius day and night. No artificial lighting or photoperiodic treatments are conducted but 'Durahuro' is forced into flowering by adding acetylene. Highest temperature resistance is 40 degrees Celsius, the lowest is 5 degrees Celsius. Direct sunlight has to be avoided because it causes burning of the leaves. The following fertilizer is added: 1 part nitrogen, 0.5 parts phosphor. 3 parts Kalium and 0.2 parts Magnesium. Water should not contain too much salts. From the start of tissue culture it takes five years to produce a commercial plant. The amount of time needed to produce an inflorescence depends on the amount of acetylene that is added. The inflorescences have a tenability of up to six months depending on the environment they are grown and kept in.

Color references are made to The Royal Horticultural Society Colour Chart (R.H.S.), except where general colors of ordinary significance are used.

Propagation: Tissue culture.

Plant:

*Form.*—Upright, leaves in basal rosette.

*Height.*—Average: 46 cm.

*Diameter.*—Average: 50 cm.

*Growth habit.*—Upright, growth moderate.

Foliage:

*Size.*—Leaves have an average length of 29 cm and an average width of 3.5 cm (measured at the middle of the leaf).

*Shape.*—Linear, tips acute to long apiculate.

*Margin.*—Entire.

*Surface texture.*—Smooth, glossy.

*Leaf color.*—Upper side: Green to yellow-green; between RHS 137A and RHS 147A. Under side: Yellow-green; RHS 146A to RHS 147A, sparcely striped vertically at the base: greyed-red; RHS 178A to RHS 178B.

Bracts:

*General shape/arrangement.*—Lanceolate, arranged alternately, tips horizontally or bent very slightly downwards in an average angle of 10°.

*Scape bracts.*—Number: Average 7. Length: Average 16 cm. Width: Average 3.4 cm. Margin: Entire. Apex: Acute. Color: Upper side yellow-green RHS 147A, tinged with greyed-orange RHS 177A, tips dark reddish-yellow-green closest to between RHS 147A and RHS 187A, base red RHS 47A; under side greyed-orange to yellow-green in between RHS 148A and RHS 177A, tips greyed-red RHS 178A. Texture: Smooth, moderately glossy.

*Primary bracts.*—Number: Average 10. Length: Average 13.2 cm. Width: Average 3 cm. Margin: Entire. Apex: Acute. Color: Upper side red RHS 47A, tips greyed-purple RHS N186C, base yellow-green RHS 146C; under side red RHS 42A, tips greyed-purple between RHS 187A and RHS 187B, base yellow-green between RHS 152A and RHS 152B. Texture: Smooth, moderately glossy.

*Floral bracts.*—Number: Average 6. Length: Average 10.4 cm. Width: Average 2.5 cm. Margin: Entire. Apex: Acute. Color: Upper side red RHS 47A, base yellow-green RHS 146C, under side red RHS 42A to RHS 42B, base yellow-green between RHS 152A and RHS 152B. Texture: Smooth, moderately glossy.

Inflorescenc:

*Borne.*—Solitary upright inflorescence.

*Individual flowers.*—Each inflorescence consists of an average of 9 individual flowers.

*Perianth.*—One large petal, lanceolate, folded, average length 5.5 cm, average width 6 mm, outer color red RHS 42 A, base green RHS 144A; inner color red RHS 47D, base yellow-green between RHS 145A and RHS 145B; rest of the perianth consists of 3 petals, lanceolate, average length 3.2, average width 3 mm, white RHS 155C, top light red RHS 38D.

*Time of blooming.*—Summer.

*Lastingness of the inflorescence.*—Up to 6 months.

Reproductive organs:

*Ovary.*—Average length 8 mm, average width 3 cm; yellowgreen RHS 145D, oblong shape.

*Style.*—1, average length 2.2 cm, white RHS 155C.

*Stigma.*—Average length 2 mm, split into 3 clavate parts, white RHS 155C.

*Stamens.*—6, attached to base of petals, average length 1.9 cm.

*Filaments.*—Average length 1.5 cm, white RHS 155C.

*Anthers.*—Average length 4 mm, basifixed, yellow RHS 4C.

*Pollen.*—Small quantity, yellow RHS 4C.

Roots: Thin, very well-branched, strong to moderately strong, color greyed-orange, RHS 165A.

Seed characteristics: No seed is developed.

Disease/pest resistance/susceptibility: No more resistant or susceptible to disease and pests than other Guzmania varieties.

I claim:

1. A new and distinct Guzmania plant named 'Durahuro', substantially as illustrated and described herein.

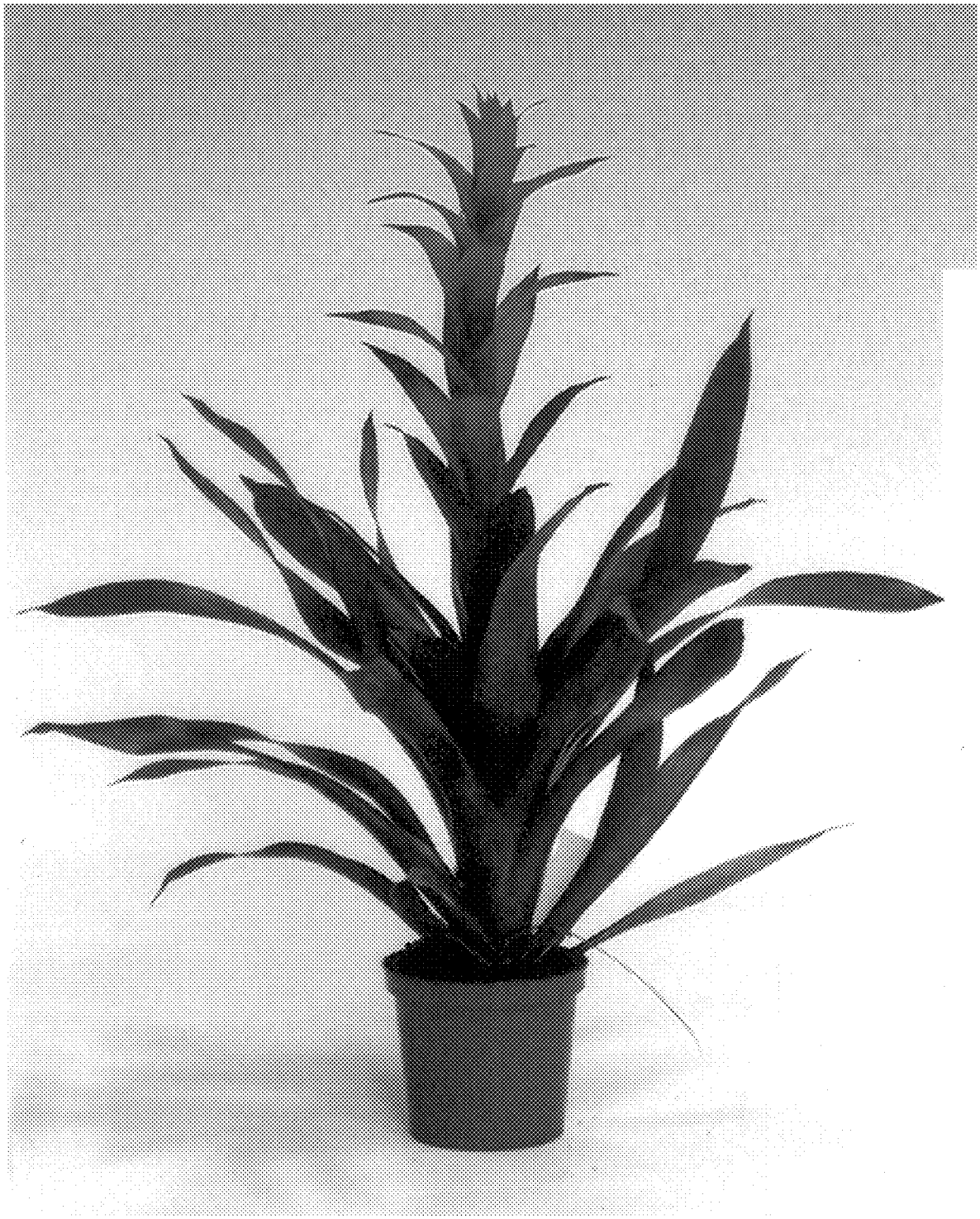

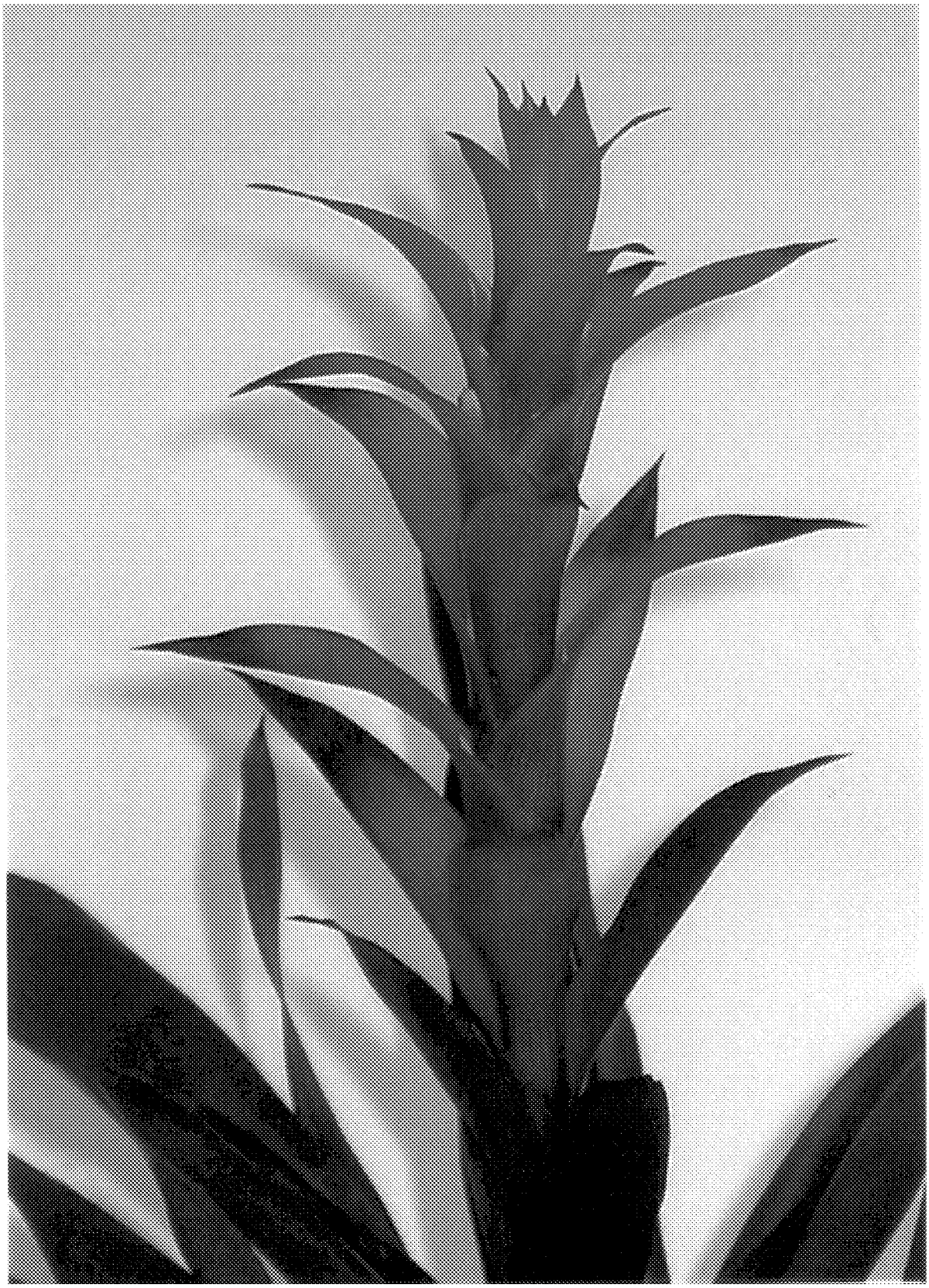

* * * * *